(12) United States Patent
Negri (10) Patent No.: US 7,103,481 B2
(45) Date of Patent: Sep. 5, 2006

(54) DEVICE FOR ANALYZING MATTER

(75) Inventor: Ricardo Martin Negri, Buenos Aires (AR)

(73) Assignee: Univeridad de Buenos Aires, Buenos Aires (AR)

( * ) Notice: Subject to any disclaimer, the term of this patent is extended or adjusted under 35 U.S.C. 154(b) by 45 days.

(21) Appl. No.: 11/055,256

(22) Filed: Feb. 10, 2005

(65) Prior Publication Data

US 2005/0178185 A1 Aug. 18, 2005

(30) Foreign Application Priority Data

Feb. 12, 2004 (AR) .............................. P040100435

(51) Int. Cl.
 *G01N 29/02* (2006.01)
(52) U.S. Cl. ...................................... 702/22
(58) Field of Classification Search ............ 702/22
 See application file for complete search history.

(56) References Cited

U.S. PATENT DOCUMENTS 6,537,802 B1  3/2003  Alocilja et al.
2004/0181346 A1*  9/2004  Sunshine et al. ............. 702/22

FOREIGN PATENT DOCUMENTS

JP  8-029412  2/1996

OTHER PUBLICATIONS

O'Connell M. et al; "A practical approach for fish freshness determinations using a portable electronic nose"; Sensors and Actuators B; Elsevier Sequoia, S.A., Lausanne, CH; vol. 80, No. 2, Nov. 20, 2001; pp. 149-154.
Rong L., et al; "A novel method for wine analysis based on sensor fusion technique"; Sensors and Actuators B, Elsevier Sequoia, S.A.; Lausanne, CH; vol. 66, No. 1-3; Jul. 25, 2000; pp. 246-250.
Kubota Corporation, JP 08 029412 A; Patent Abstracts of Japan, vol. 1996, No. 06; Jun. 28, 1996.
Cole M., et al; "Fabrication and testing of smart tongue devices for liquid sensing"; Proceedings of IEEE sensors 2002; Orlando, FL, Jun. 2002; vol. 1 of 2, conf. 1; pp. 237-241.
Winquist F. et al, "The combination of an electronic tongue and an electronic nose"; Sensors and Actuators B, Elsevier Sequoia, S.A.; Lausanne, CH; vol. 58, No. 1-3; Sep. 21, 1999; pp. 512-517.

* cited by examiner

*Primary Examiner*—Michael Nghiem
*Assistant Examiner*—Tung S. Lau
(74) *Attorney, Agent, or Firm*—Norris McLaughlin & Marcus PA (57) ABSTRACT

An electronic device for discriminating, identifying and analyzing liquid, semi-liquid and solid samples containing volatile components, by performing simultaneous evaluation of odor and taste of the samples, the device having a closable and thermally stable chamber wherein the sample to be analyzed is placed, the chamber including, in direct contact with the sample, a set of electronic sensors for sensing a non-vapor phase of the sample, a second set of sensors for sensing a vapor phase of the sample and humidity and temperature sensors, with the signals from the sensors being processed and sent to a computing platform comprising a pattern-recognizing program and/or a multi-varied-data analysis program.

20 Claims, 8 Drawing Sheets

DEVICE FOR ANALYZING MATTER

BACKGROUND OF THE INVENTION

1. Field of the Invention

The present invention relates to the field of the analysis of substances, compounds and any matter in general, and particularly refers to a portable electronic device for discriminating, identifying and analyzing liquid, semi-liquid and solid samples containing volatile components, wherein the general analysis of the matter is based on the simultaneous evaluation of several properties of the samples by a plurality of sensors, preferably sensors having a low chemical specificity, wherein the sensors provide signals that are processed in a computing platform having a pattern-recognizing program and wherein the properties may be associated to what is generally called the odor and taste of the sample. For the purposes of this description the word flavour may be understood as a combination of odor and taste of a sample.

2. Description of the Prior Art

Several electronic devices are known today for analysing those properties of any matter associated to the smell and taste thereof.

In relation to the sense of smell the devices have been developed to discriminate the samples having volatile components by detecting and recognizing the mixture components of the sample vapour, the mixture being named "odor" of the sample. Such devices are known as "electronic noses" and the employed methodology is named "artificial olfaction". Examples of such electronic noses are the devices disclosed in U.S. Pat. No. 6,598,459; U.S. Pat. No. 6,540,008; U.S. Pat. No. 6,411,905 and U.S. Pat. No. 6,319,724. Such devices are comprised of arrays of non-specific gas sensors, based in several materials with varied function principles. By the signals generated by the sensor arrays the electronic noses obtain a digital print or sign of each of the analysed odors and, through the use of multivaried-data analysis try to recognize odor patterns.

There are devices that are employed for in-situ quality analysis of agricultural products, U.S. Pat. No. 6,450,008, WO 0107907; for discriminating, by the analysis of a patient's breathing, a medicine the patient has ingested, WO 0134024, CA 2,390,261; for detecting molecular compounds having chiral structures, WO 9940423; for diagnosing pulmonary infections, U.S. Pat. No. 6,620,109; U.S. Pat. No. 6,620,107 and U.S. Pat. No. 6,461,306.

One of the main drawbacks of these devices is that they analyse only the vapour phase of the sample without resolving the problem of analysing the vapour and no-vapour phases. For example, when analysing wine, said devices are unable of analysing the features of the liquid phase per se.

Another main drawback of the above mentioned devices, such as those of U.S. Pat. No. 4,818,348; U.S. Pat. No. 6,620,107 and U.S. Pat. No. 6,537,802, is that vapour from the samples are suctioned or draught from a place where the sample is placed and the vapour is carried to a chamber containing the sensors. In the device disclosed in U.S. Pat. No. 6,397,658 the vapours from the sample are suctioned and collected, by adsorption, in an adsorbing material, then the vapours are desorbed and finally transported by nay draft means to a chamber containing the sensors. The device disclosed in U.S. Pat. No. 6,467,333 employs a similar method. These processes are based in separating the odor from the sample which separation no only needs of two chambers, one for the sample and the other one for containing the array of sensors, but also provide a clear and remarkable separation between the vapour phase and the no-vapour phase.

There are also devices that get inspiration from the sense of taste. Their operation is based in the analysis of a non gaseous phase of a sample using sensor arrays. To this purpose, sensors based on noble metal electrodes may be employed, with the same electrodes producing different electrical potentials according to the substances contained in the sample. It is also known the use of electrodes employing PVC membranes modified with organic macromolecules, surface wave sensors and other devices that modify their electrical or optical properties according to the substances in contact to the sensors. In such cases where a global analysis of the sensors signals can be done such devices are named "electronic tongues". Such devices are disclosed in U.S. Pat. No. 6,610,367; U.S. Pat. No. 6,627,154 and U.S. Pat. No. 6,541,617, for example.

The main drawback of the electronic tongues is that these devices are only able to analyse the non-vapour, or non gaseous, phase of the sample, therefore the information contained in the vapour phase is completely disregarded. Even when the sample sensed in the electronic tongue could be brought to an electronic nose for further analysis, said analysis would not be done under the same environment conditions under which the analysis in the electronic tongue has been done and, in addition, the time passed between the two analysis leads to another disparity in the sample conditions.

In virtue of the present state of the art it would be very convenient to have a device capable of carrying out the simultaneous analysis of odor and taste in a sample in order to prevent variations in the sample conditions.

SUMMARY OF THE INVENTION

It is therefore an object of the present invention to provide a device capable of analyzing and identifying samples by globally and simultaneously sensing the odour (generated by the volatile components) and the taste (generated by the non-volatile components) of a liquid, semi-solid or solid sample, with the device permitting to discriminate the samples by means of a pattern-recognizing method, without the analysis requiring of the separation of vapour and non-vapour phases and without the need of preparing the sample prior to the analysis.

It is a further object of the present invention to provide an electronic device for discriminating, identifying and analyzing liquid, semi-liquid and solid samples containing volatile components, by performing simultaneous evaluation of odor and taste of the samples, the device having a closable and thermally stable chamber wherein the sample to be analyzed is placed, the chamber including, in direct contact with the sample, a set of electronic sensors for sensing a non-vapor phase of the sample, a second set of sensors for sensing a vapor phase of the sample and humidity and temperature sensors, with the signals from the sensors being processed and sent to a computing platform comprising a pattern-recognizing program and/or a multivaried-data analysis program.

It is still another object of the present invention to provide a device for analyzing and simultaneously evaluating odor and taste of matter containing volatile components, the device comprising:

a chamber for receiving and containing a matter sample under stable thermal conditions;

at least one first sensor arranged in the chamber for sensing a vapor phase of the sample;

at least one second sensor arranged in the chamber for sensing a no-vapor phase of the sample;

at least one third sensor arranged in the chamber for sensing temperature into the chamber;

at least one fourth sensor arranged in the chamber for sensing humidity into the chamber;

an electronic circuit connected to said sensors for a simultaneous and real time analysis of vapour and no-vapour phases of the sample, and a computing platform that comprises at least one pattern-recognizing program and/or a multivaried-data analysis program, wherein the electronic circuit simultaneously acquires data from the sensors and transmits the data to the computing platform.

It is a further object of the present invention to provide the above described device wherein the chamber is a closable container that may be closed to form a sealed and watertight chamber, such as a portable chamber, for containing the sample and the sensors are mounted in at least one wall of the container, with the container comprising a first portion, such as an upper portion, and a second portion, such as a lower portion, and both container portions are adjustably coupled to define at least a maximum distance position, a minimum distance position and a contact position between the sample and at least part of the sensors, wherein the first and second portions of the container may be threadably connected to regulate said positions between the sample and at least part of the sensors or at least one of the first and second portions of the container has a sliding connection to regulate said positions between the sample and at least part of the sensors.

It is still another object of the present invention to provide the above described device wherein at least one of the sensors or the sample is mounted in a mechanism for moving the at least one sensor or the sample towards to or away from the sample, with the device also including an agitator arranged in the chamber for agitating the vapour phase, a tray in the chamber for containing the sample and temperature control means connected to the chamber to heat the chamber, wherein the chamber may be at least partially supported onto at least one peltier-type plate to thermally control the chamber and wherein the at least one first sensor and the at least one second sensor are of type selected from oxide-metal semiconductors, conductive polymers, oligomers, piezoelectric materials, surface acoustic wave sensors, noble metal electrodes, ion-selective electrodes, glass electrodes and the like and wherein the at least one third sensor is of the type selected from thermistors, laser sensors, PT100 and thermocouples.

It is still another object of the present invention to provide the above described device wherein the electronic circuit comprises a regulated voltage source, load resistors connected to the sensors for sensing the vapour phase of the sample, high impedance adaptors connected to the sensors for sensing the no-vapour phase of the sample, and a control circuit for control, acquisition and transmission of data, the control circuit being connected to the at least one load resistor and including at least one high impedance adaptor connected to the sensors for sensing the no-vapour phase of the sample and wherein the control circuit comprises at least one multiplexor connected to an analogical/digital converter that is connected to a micro controller, a clock circuit defining a timer circuit, and an adaptor circuit for adapting to a computer communications port and connected to said micro controller and wherein the computing platform is communicated with the electronic circuit by means of a wire type or a wireless type connection.

It is still another object of the present invention to provide the above described device, wherein the chamber is a portable chamber that comprises an inverted cup for introducing into a liquid mass to be analyzed, with the at at least one first sensor being arranged at the top of the chamber to prevent the sensor to enter into contact with the liquid, wherein the at least one second sensor and the at least one third sensor extend from the top of the inverted cup for entering into contact with the liquid when the cup is introduced into the liquid mass, and wherein the at least one fourth sensor is arranged into the chamber to prevent the contact thereof with the liquid.

The above and other objects, features and advantages of this invention will be better understood when taken in connection with the accompanying drawings and description.

BRIEF DESCRIPTION OF THE DRAWINGS

The present invention is illustrated by way of example in the following drawings wherein.

DESCRIPTION OF THE PREFERRED EMBODIMENTS

Now referring in detail to the invention, the same refers to the field of the analysis of matter, either solid, semisolid, liquid, semi-liquid and mixtures thereof, and particularly refers to the devices generally known as electronic noses and tongues which, according to the invention, are integrated in only one device or apparatus for analyzing and evaluating, in a simultaneous manner, odor and taste of matter containing volatile components.

Figure 1:
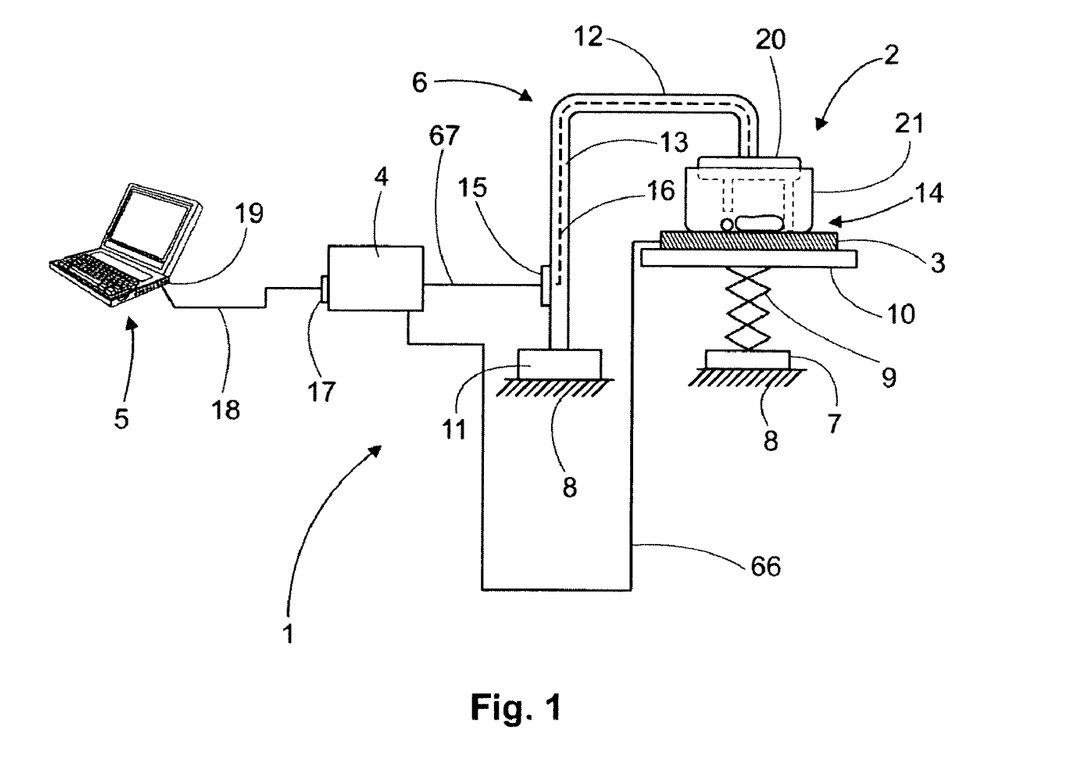
FIG. 1 diagrammatically shows the inventive device and its main components.

The inventive device is generally illustrated in FIG. 1 wherein the electronic device is indicated by reference number 1 and shown as mainly comprising a chamber, indicated by reference number 2, for receiving and containing a matter sample or samples, preferably under stable thermal conditions, a "Peltier" plate 3 supporting the chamber, an electronic circuit or box 4, including a control circuit for control, acquisition and transmission of data, and personal computer PC or notebook, indicated by reference number 5, with one or more programs for recognizing patterns. It is clear that any computing platform may be provided in replacement of said PC or notebook, such as a "handheld", "palmtop" or any other type of computer capable of housing the above indicated software.

Chamber 2 may be mounted in a vertical support, indicated by reference number 6, that is supported in a stationary surface 8 by means of a base 11. An arm 12 forming part of vertical support 6 keeps chamber 2 spaced apart from a vertical column 13. Support 6 provides a firm mounting of chamber 2 and, due to its construction features, permits the easy operation for introducing a sample "S", FIG. 2, or samples.

Temperature control means, such as at least one Peltier-type plate 3 is in contact with chamber 2 for thermally controlling the chamber. Peltier plate 3 is electrically fed by electronic circuits, either in box 4 by bipolar wires 66 or in an independent box (not shown), to heat or cool chamber 2. Support 6 is mounted at its bottom part in a stationary surface 8 and comprises an articulated mechanism 9 supported in flat base 7 and that provides platform 10 and peltier plate 3 with support and a lifting or vertical movement up to a height contacting a portion, preferably a bottom portion 14, of chamber 2. Other temperature control means may be employed instead of Peltier plate 3, such as a water jacket with heated or cool water circulating around chamber 2 to control its temperature.

As to the connections of chamber 2 the same is electrically connected to box 4 through wires 16 running inside arm 12 and coming out arm 12 through exit 15. All the cables out of arm 12 are indicated by reference number 67. Box 4 comprises a DB9-type connector 17 which in turn is connected to a RS232 type communication wire or cable 18. The opposite end of said communication cable 18 is connected to a series communication port 19 provided in computer 5.

Figure 2:
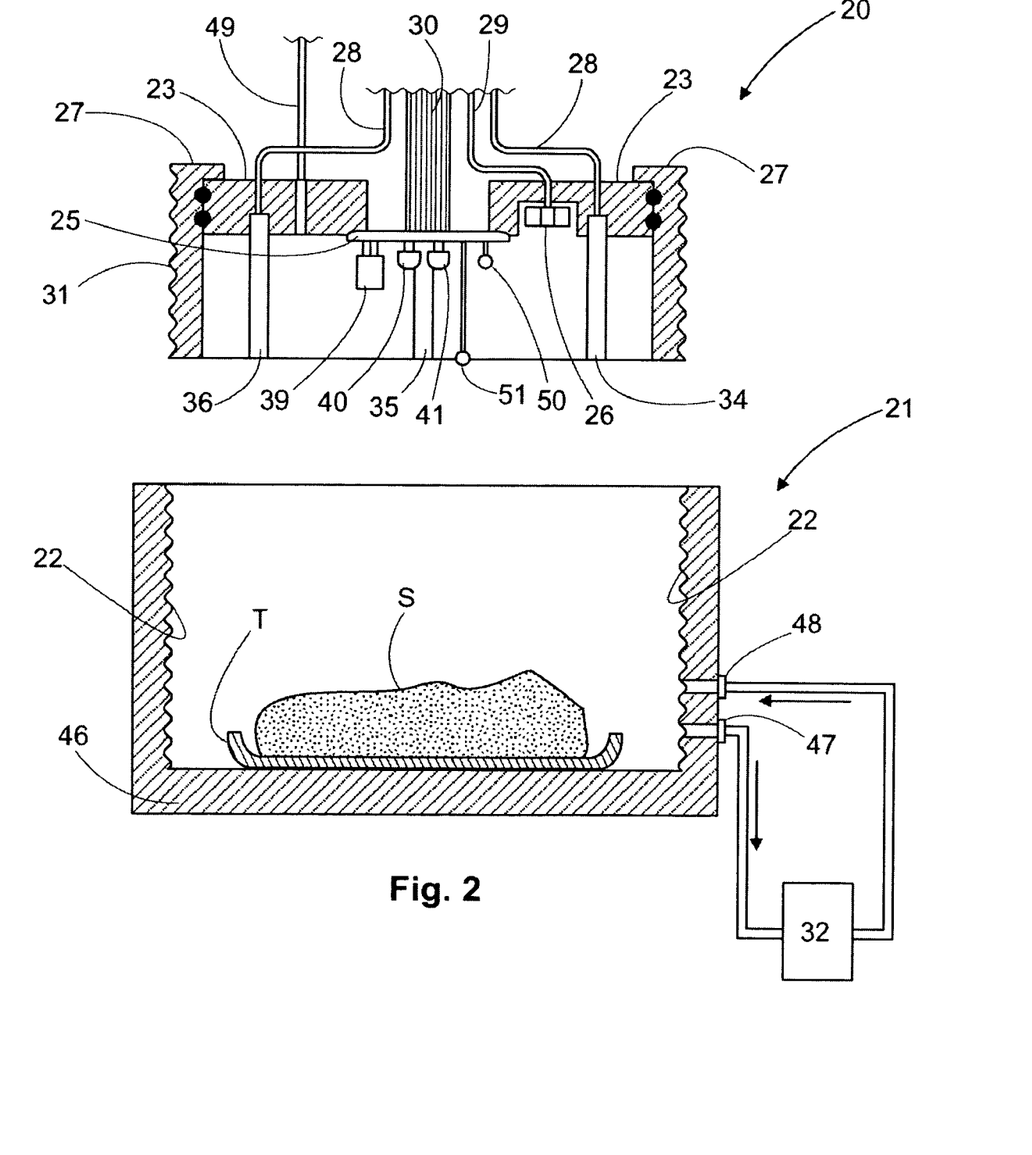
FIG. 2 is a side elevation and partial cross sectional view of the chamber for containing the samples according to the invention.
Figure 3:
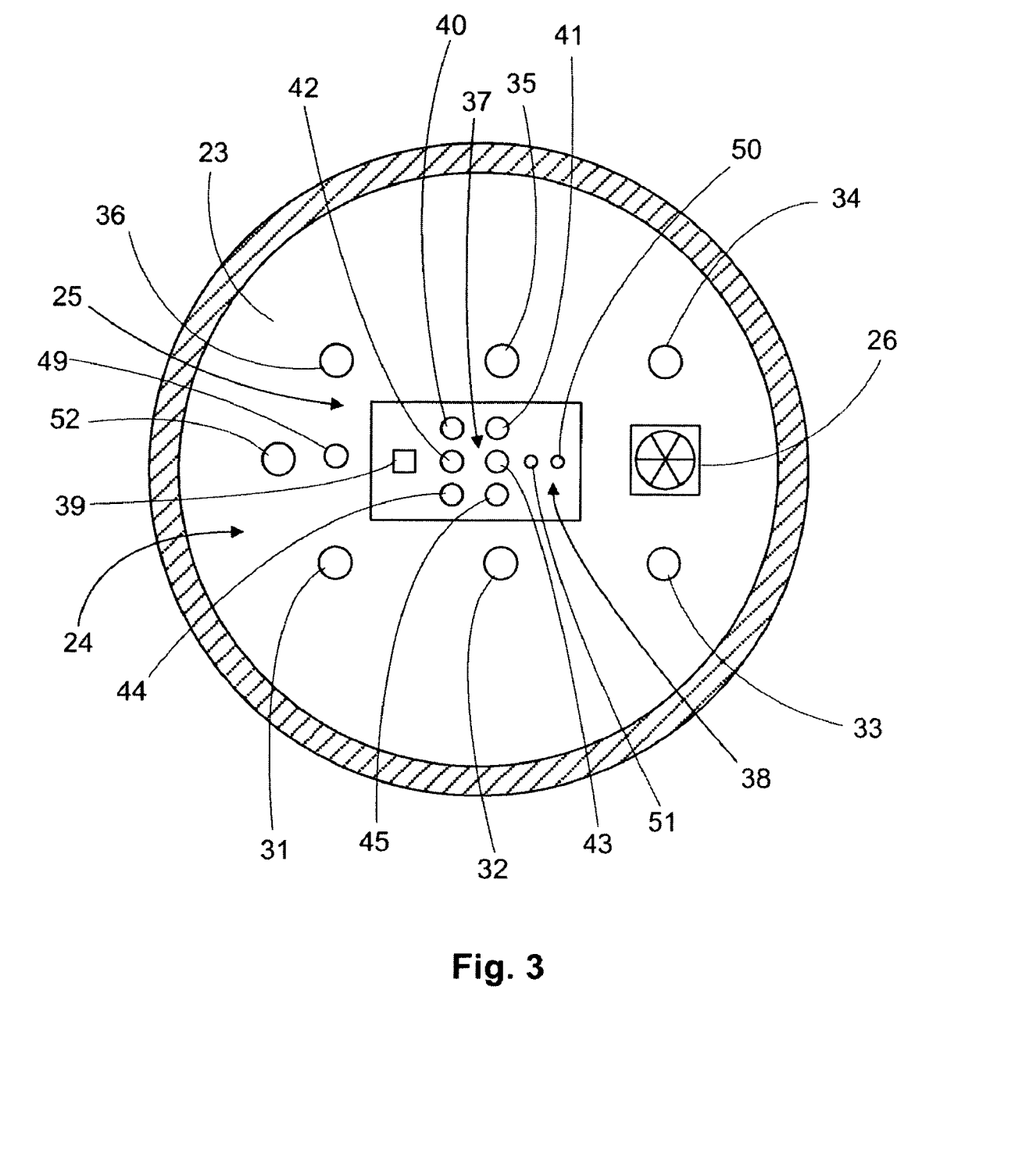
FIG. 3 is a bottom plan view of the upper lid of the chamber of FIG. 2.

Making reference to FIGS. 2 and 3, construction and functional features of chamber 2 are illustrated. Chamber 2 is basically comprised of two parts or portions adjustably coupled, such as a first portion, such as an upper portion 20, and a second portion, such as a lower portion 21, which portions form a sealed and watertight chamber when both portions are closed to each other. Upper and lower portion 20, 21 are of a substantially cylindrical shape and may be made of any appropriate material. Portion 21 is preferably made of aluminum or stainless steel and portion 20 may be made of combination of metal, such as aluminum, and plastics or resin materials in such a manner that the portion where the sensors are mounted is made of plastics or resins. For instance, as will be disclosed below, upper wall 23 may be made of plastics, such as "Derbin". The outer cylindrical surface of portion 20 has all around its surface a plurality of screw threads for threadably connecting to a thread 22 in an inner surface of bottom portion 21. As mentioned above, portion 20 has a movable upper wall or surface 23 that is sealed against portion 20 by any appropriate means such as ring-seals as illustrated in order that wall 23 can sealably slide into potion 20. Chamber 2 may be a stationary chamber or container, a desktop chamber or a portable chamber.

Within chamber 2 there is at least one first sensor 37 for sensing a vapor phase of the sample, at least one second sensor 24 for sensing a no-vapor phase of the sample, at least one third sensor 38 for sensing temperature into the chamber, at least one fourth sensor 39 for sensing humidity into the chamber. As disclosed below, these components are connected to an electronic circuit connected to said sensors for a simultaneous and real time analysis of vapour and no-vapour phases of the sample. In addition a computing platform that comprises at least one pattern-recognizing program and/or a multivaried analysis program is also provided and the electronic circuit simultaneously acquires data from the sensors and transmits the data to the computing platform.

More particularly, several sensors 24 for detecting the non-vapour phase of sample S, a circuit 25, such as an electronic or printed circuit, and an agitator 26 for agitating or stirring a vapour phase of the sample, are mounted in the chamber, preferably in upper wall 23, and extend substantially perpendicular to upper wall 23 and towards portion 21. Said electronic devices are connected to box 4 by a plurality of cables that may be of different types according to features of the signal transmitted by each respective cable. Regarding the no-vapour phase sensors 24 the connection is made by a respective coaxial cable 28 per each one of the respective sensors 24, a bipolar cable 29 is employed for the agitator element and the connection for the printed circuit is made by a flat cable.

The group of no-vapour-phase sensors 24 may comprise six or seven sensors, with an additional one for reference. Sensors 24 preferably comprise potenciometric ion-selective-electrodes 31 based on polymeric plastized membrane ISE-PPM with higher selectivity to chloride (Cl$^-$), an ISE-PPM with higher selectivity to sulphide (S$^{-2}$) 32, an ISE-PPM with higher selectivity to NH$_4^+$ 33, a pH glass electrode 34, an ISE-PPM with higher selectivity to iodine (I$^-$) 35, an ISE-PPM with higher selectivity to potassium (K$^+$) 36 and a reference electrode silver/silver chloride (Ag/AgCl, 3M) 52. Other additional sensors may be employed such as an ISE-PPM (not illustrated) with higher selectivity to other ions. Said sensors are of substantially cylindrical, however the constructive features of the sensors may vary according to the given needs such as the sample shape and consistency. Any skilled in the art my employ, for example, sensors with a rounded tip, a sharp tip, a needle tip, a "fork" type tip, a punch tip with substantially polygonal section and the like.

A plurality of vapour phase sensors 37, two temperature sensors 38 and a humidity sensor 39 are connected, by welding for example, to circuit 25. The preferably twelve vapour phase sensors are made by the firm Figaro Inc, and are of the following models: TGS 825 (reference 40), TGS 832 (reference 41), TGS 882 (reference 42), TGS 2610 (reference 43), TGS 2611 (reference 44) and TGS 2620 (reference 45). For clarity purposes only six sensors have been illustrated but the remaining six sensors may be models TGS 813; TGS 880; TGS 826; TGS 816; TGS 842; TGS 823; TGS 800 y TGS 831. The temperature sensor indicated by reference number 50 is placed close to the surface of the printed circuit, this sensor is known by the trademark "National", LM35 Model, and the remaining temperature sensor 51 has longer terminals that permit the sensor to stay at more spaced apart from the surface of the printed circuit, that is, the direct contact of the sensor and the sample is permitted, in like manner as the non-vapour phase sensors 37 are. This second temperature sensor is a generic thermistor.

While determined sensors have been described above, sensors 24 for sensing the non-vapour phase of the sample and sensors 37 for sensing the vapour phase of the sample may be of any other types, for instance anyone selected from the group consisting of oxide-metal semiconductors, conductive polymers, oligomers, piezoelectric materials, surface acoustic wave sensors, noble metal electrodes, ion-selective electrodes, glass electrodes and the like. In like manner, the third sensor or temperature sensor may be of the type of thermistors, laser sensors, PT100 or thermocouples.

As better shown in FIG. 2, the two first and second portions 20 and 21 of the chamber or container 2 are adjustably coupled to define at least a maximum distance position, a minimum distance position and a contact position between the sample and at least part of the sensors. Therefore, the first and second portions of the container are threadably connected, through threads 22, 31, to regulate said positions between the sample and at least part of the sensors. As indicated above, at least one of the first and second portions of the container, namely wall 23 of portion 20, has a sliding connection to regulate said positions between the sample and at least part of the sensors. All these constructions form a mechanism for moving any desired sensor towards to or away from the sample. Therefore it is clear that the sensors or the sample is mounted in a mechanism for relatively moving the at least one sensor and the sample towards to or away from each other.

Sample S is preferably placed and contained in a tray "T" that is placed in a lower or bottom wall 46 of the chamber. Tray T may have any desired configuration depending on the type and size of the sample, as well as if sample is liquid, solid, semi-solid, etc. When sample S is in chamber 2, portion 20 is threadably connected to threads 22 and when both portions 20, 21 are connected wall 23 is slidably moved in portion 20 and lowered up to the non-vapour phase sensors, if desired, enter into contact with the sample, then portion 20 is rotated again and adjusted in position up to having wall 23 seated against an upper edge 27 of portion 20.

Preferably, threads 22 formed in the entire inner surface of lower portion 21 and threads 32 formed in the entire outer surface of upper portion 20 have the same mechanical characteristics to have a good coupling therebetween. This permit both portions to rotate relative to each other, therefore, according to the turns that one portion, preferably portion 20, is rotated relative to the other, preferably portion 21, the height, and even the contact, of the non-vapour phase sensors 24 and temperature sensor 51 relative to the sample may be adjusted, as well as the proximity of sensors 37, temperature sensors 38 and humidity sensor 39 is also adjusted relative to the sample. Alternatively, portion 20 may be manufactured with wall 23 fixed or stationary relative to the remaining part of portion 20. In this event, when sample S is placed into potion 21, portion 21 will be rotated relative to portion 20 and portion 20 will remain stationary.

The material employed to manufacture upper portion 20 must permit the mounting of the sensors and prevent them from any damage, as well as this material must not contain volatile components, that is it must not "smell", and it must be easily machined. Preferably, a substantially plastic material is employed for the construction of at least part of portion 20, such as Teflon, Derbin and the like. Lower portion 21 preferably has no sensors mounted therein, however, it must be made of a good thermal conductor material in order to thermally connect the Peltier plate with the sample and it must resist to the chemical attack of the components forming part of the sample. Because of the above questions aluminium is employed for the construction of portion 21. While determined materials have been indicated as employed in the device of the present invention, it is clear that any person skilled in the art may employ other materials for satisfying the already known needs and other future needs.

A determined number, types and arrangements of sensors in the chamber have been indicated above as preferred for the exemplary configuration of the present invention however it is possible to employ different types of sensors, change the number of sensors and arrange the sensors in different ways in the chamber, all this for satisfying different needs and for adapting the device to several sizes and number of samples and uses. As an example, it would be possible to employ a laser sensor for sensing temperature in the non-gaseous phase that, while costlier than a thermistor, does not require the direct contact with the sample; in like manner more than twelve (12) non-vapour or non-gaseous sensors may be employed, which sensors are based on function principles other than potentiometry, for instance, sensors operating on the basis of colorimetry, amperometry, voltametry and the like may be included. Regarding the arrangement of the sensors, in the preferred embodiment of the invention, the sensors are fixed in a stationary manner in at least one of the walls of the chamber for samples, however, in an exemplary embodiment, at least part of said sensors may be mounted on a mechanism comprising hinges, movable arms and the like, to permit the movement of the sensors along at least one axis in the space in a manner that is possible to place the sensors as desired relative to the sample. Another example of how to mount the sensors is to have them fixedly mounted on at least one of the chamber walls with a mechanism, such as lifting mechanism 6 of FIG. 1, for moving the sample along at least one axis in the space. Other possibilities are also considered, with the above ones described above being only examples. It should be considered that any expert in the art may find modifications in the device of the present invention without departing from the essence of the invention.

If the sample is a liquid it may be desirable to simultaneously subject the sample to other analysis, such as flow injection analysis or chromatography for example. In these cases the sample, or part thereof, should be removed and recycled into the chamber again to not alter the sample and the analysis condition. To this purpose, chamber 2, and preferably portion 21, may be provided with an outlet port 47 and an inlet port 48 connected to an analysis device 32 such as a flow injection chemical analyzer that receives a portion of the liquid sample from outlet 47, analyses the sample without altering the same and resend the sample to the chamber through port 48.

For taking vapour samples upper portion 20 is provided with a sampling conduit 49 for removing gas sample from sample S to send the same to a gas chromatographer for chemical analysis, for example. Conduit 49 may serve also for solid phase micro extraction for analysis in activated carbon cartridges.

Figure 4:
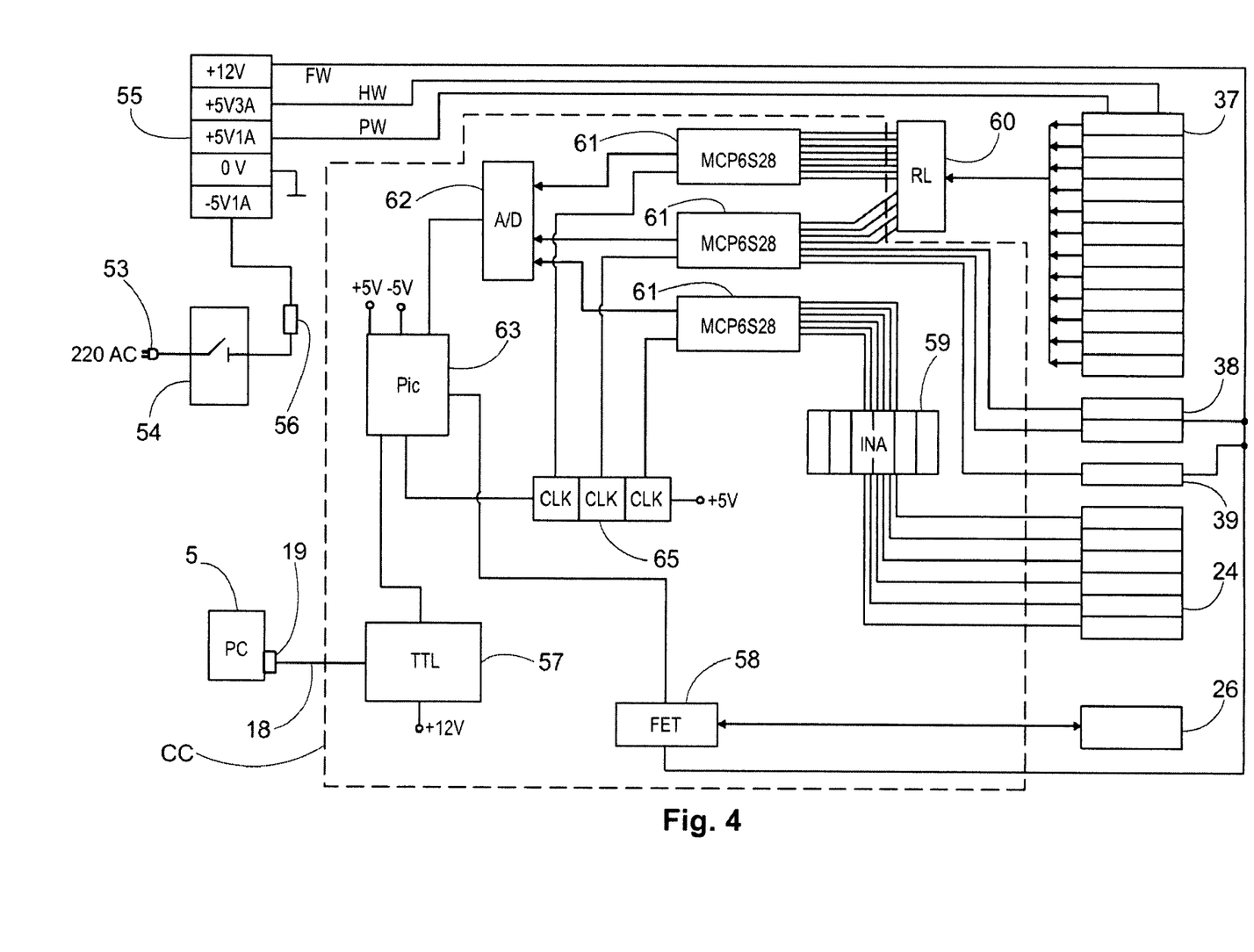
FIG. 4 is a block diagram showing the arrangement and connections of the electronic components of the inventive device.

Making now reference to FIG. 4 a block electrical circuit or diagram is illustrated showing the several electronic components forming part of the invention. The inventive device may be connected to the 220 AC supply by means of a connector 53. By actuating a switch 54 the input from a regulated voltage source 55 is energized. A fuse 56 provides electrical protection for preventing any short circuit or overcharge in the device. Source 55 provides regulated tensions and feedings of +12 VDC, +5 VDC 3 A, +5 VDC 1 A, 0V and −5 VDC 1 A. FW wire is for feeding +12V to an integrated adaptor circuit TTL/RS232, indicated by reference number 57, to temperature sensor 38, to a humidity sensor 39 and to fan 26 through transistor FET60N06 58. Vapour sensors 37 are provided with heating by wire HW and with polarization by wire PW.

The integrated adaptor circuit TTL/RS232 is a MAX (trademark registered) adaptor, model 232ACPE, and the humidity sensor 39, is a Honeywell (trademark registered), model HIH-3610series. Temperature sensor 38 is preferably comprised of two sensors, one for sensing the temperature of the liquid phase of the sample and one for sensing the temperature of the gas phase of the sample. Thus, block 38 is depicted as comprised of two boxes or portions.

Vapour-phase sensors 37, namely the sensors for detecting the vapour phase or gas from the sample, preferably comprise 12 sensors indicated as twelve boxes in block 37 and are semi-conductors basically comprised of tin dioxide doped with several components in several proportions according to the model of a particular sensor. When the semi-conductor is subject to a polarization the electrical current is conducted and, according to the employed doping components and their proportions, the electrical conductivity is varied. This is why the employed sensors 37, as stated preferably 12 sensors, are of different models because upon the presence of a determined gas and/or vapour twelve output variables are obtained, that is one value per sensor. Otherwise, if the sensors would be of the same characteristics only one value repeated twelve times by the twelve sensors would be obtained. Each sensor employs an inner electric resistance, fed by HW, for heating the semiconductor and increasing the energy of the electrons in the semiconductor, thus enhancing the electrical conductivity. This is done to reduce the measuring threshold and increase sensitivity. As to the non-vapour sensors 24, that is the sensors for sensing the non-vapour or non-gas phase from the sample, the principle of operation thereof is completely different as long as it is based in potentiometry, that is, in the measuring of electrical potential without the extraction of significant current. Sensors 24, illustrated as comprising 6 sensors indicated by six boxes in block 24, generate, according to the ions in the non-vapour phase of the sample, potential variations relative to the potential-reference electrode 52, not illustrated in FIG. 4. Basically the effect is similar to that one occurring in electrical batteries. A high impedance adaptor 59 for each sensor 24 receives said voltages and therefore has a high input impedance because the current circulating between electrodes 24 and adaptor 59 must be minimal, otherwise the measured potentials would be markedly reduced close to a value of 0 Volt. The adaptors 59 are represented by divisions or boxes in only one block 59 for clarity purposes.

Energy is provided from +5 VDC output to all the integrated circuit forming part of the electronics of the device, except for the integrated adaptor circuit TTL/RS232 57. This +5 VDC output is also fed to inner resistances for heating the vapour phase sensors. Thus, sensors 37 receive a double feeding, for heating inner resistances, one per sensor, and for the semiconductor material forming part of the sensing function of sensor. For achieving the highest electrical stability and due to the difference of consumption by the heating resistances and sensors per se, both electrical feeding are made by separate, generally by using different tension regulators as in this case.

Each vapour phase sensor 37 is connected in series to a load resistance 60 forming a resistive divisor. The end of such resistive divisor corresponding to the semiconductor of the gas or vapour sensor is energized, as indicated above, by 5 VDC, with the end of the divisor corresponding to the load resistance being connected to 0V. Therefore, the voltage drop in the load resistance varies according to the semiconductor conductivity. The signal from the measure of the respective sensor is taken at the electric connection between the load resistance and the semiconductor and it is sent to one of the inputs of at least one programmable gain amplifier model MCP6S28, indicated by reference number 61. There are preferably three amplifiers 61 for receiving the signals from the sensors 37, 24, 38 and 39.

The electric signals from the non-vapour sensors 24 are directly fed to the inputs of multiple input high impedance adaptors INA16C, one per sensor 24, identified by reference 59, then the outputs from adaptors 59 are electrically connected to the inputs available in another one of amplifiers 61. Humidity sensor 39 has three terminals, two for feeding (+12 VDC and 0V) and the third one is for obtaining a tension or voltage value that is lineal and proportional to the relative humidity in the room the sensor is operating. The signal from humidity sensor 39 is fed to another one of amplifiers 61. The outputs from amplifiers 61 are fed to an analogical/digital converter 62 that operates to digitalize the analogical signals coming from the amplifiers. Converter 62 is in turn connected to an input terminal of a microcontroller PIC16F877-04, indicated by reference number 63. Microcontroller 63 has a program in assembler language, with the program being designed according to the necessary functions that are desired to be carried out. Amplifiers 61 are controlled by microcontroller 63.

An electronic circuit clock 65 based in a 4 MHz piezoelectric crystal model XL1 is employed for emitting the clock signal under which the microcontroller 63 and amplifiers 61 are operated. Indeed, there are three clocks 65 indicated by three boxes in block 65 with each clock connected to each amplifier 61.

Once the signals are inwardly digitalized the same are processed by the microcontroller and ordered in series data packets of transmission and sent to converter TTL/RS232 indicated by reference 57. The output of converter 57 is connected to series communication port 19 of the computer 5, or computing platform, by a communication cable RS232, indicated by reference 18. Alternatively, computer 5 and electronic circuit may be connected by a wireless connection. In this manner, the computer with the pattern recognizing software receives the data to be processed.

In the circuit of FIG. 4, a control circuit for control, acquisition and transmission of data is defined and indicated within the phantom line "CC", with the above mentioned components, within phantom box CC forming part of this control circuit.

The software hosted in the computer operates according to three functions: it communicates to the microcontroller, it provides a graphic inter-phase with the user and it executes algorithms for recognizing patterns. In the exemplary embodiment of the present invention the software was designed in Visual Basic language, however it can be made in any other language such as Visual C, Visual Fox and the like provided that the needs of the user are satisfied. The communication with the microcontroller 63 is based in the reading of the signals obtained by the microcontroller from the sensors and in the transference of these signals both to the graphic inter-phase and to the software for recognizing patterns. The microcontroller also controls the vapour-phase agitator or fan 26, the sampling frequency and the acquisition average time of A/D converter 62. This requires, from the programming point of view, cooperation between the software in the computing platform 5 and the software in microcontroller 63.

Figure 5:
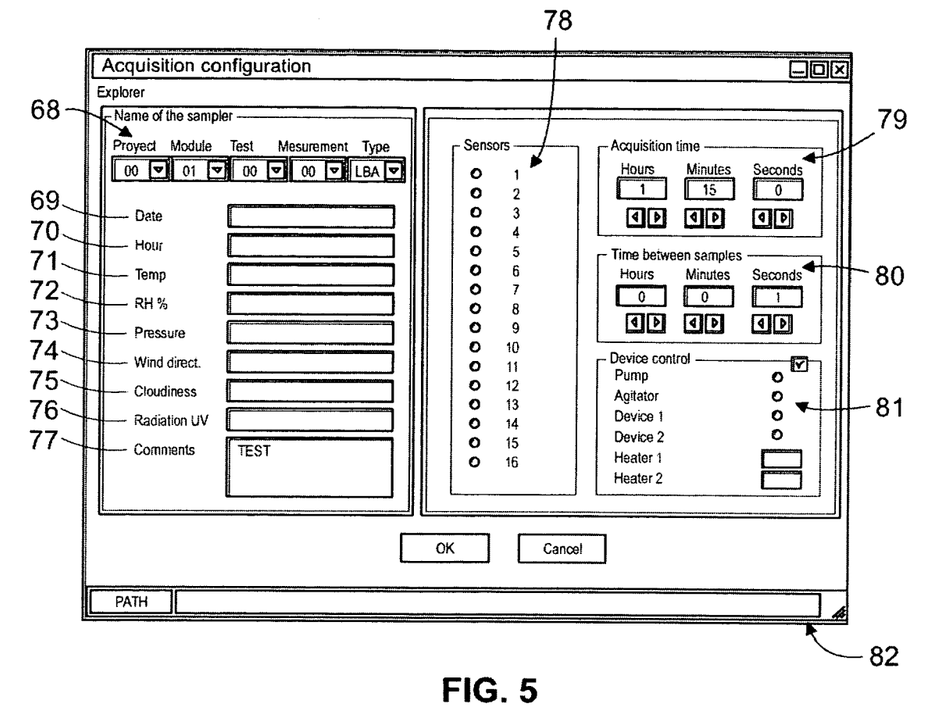
FIG. 5 is a front view of a computer screen showing a configuration page of the software that is used by the user to operate the device according to the invention.

Making now reference to FIG. 5, a configuration screen or display of the inventive device is shown. It is possible to enter several parameters in boxes or windows of the screen, such as identification of sample 68, date 69, hour 70 when the test is made, temperature 71, relative humidity 72, room pressure 73 and comments 77. Some of said parameters, like date 69, hour 70, temperature 71 and relative humidity 72 may be entered automatically by the computer from the data retrieved from the system and sensors. It is also possible to indicate which sensors or the type or kind of sensors that are to be employed in the analysis of a determined sample, and to check or not the text corresponding to a determined sensor in the sensors window 78. Other parameters to be configured are the total acquisition time 79 and the record frequency 80. The total acquisition time is the total time that the test will take and the record frequency is given by the period of time in which the signals acquired by the sensors are averaged for recording into the computing platform. By the device control window 81 it is possible to turn on and off desired devices such as agitator 26.

As an example, to control the turning on and off of the agitator 26 a signal is sent by computer 5 via series port 19 to the signal converter TTL/RS232, indicated by reference number 57. Converter 57 converts the signal and feds the converted signal into microcontroller 63, then microcontroller 63, via one of its outputs, energizes transistor 58 which is electrically saturated and permits the pass of feeding +12 VDC supply to agitator 26.

Figure 6:
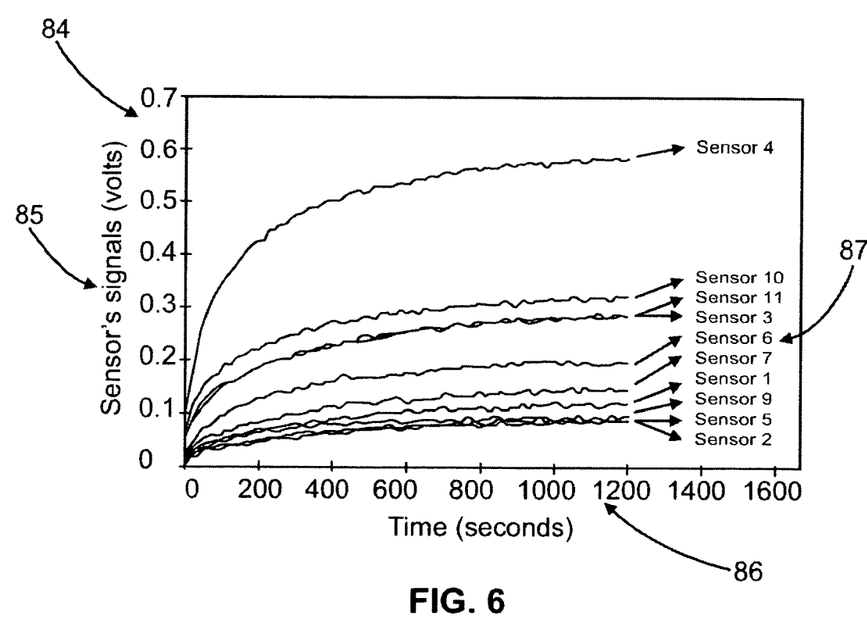
FIG. 6 is a front view of a computer screen showing another image containing the signals provided by the sensors according to the acquisition time.

During the process of analysing a sample, once the parameters have been configured into the configuration screen shown in FIG. 5 with reference 82, the graphic inter-phase shows a graph or screen like the one shown in FIG. 6. Said graph shows, in axis 84, the signals from all the sensors by curves representing the signals from sensors 85 versus the acquisition time, with the acquisition time being shown in axis 86, typically in a rate of between two and ten minutes, averaged during a given sampling time, typically three seconds. The curves appear in different grey tones and reference 87 indicates the different tones and their correspondence with each curve which in turn corresponds to each sensor.

Figure 7:
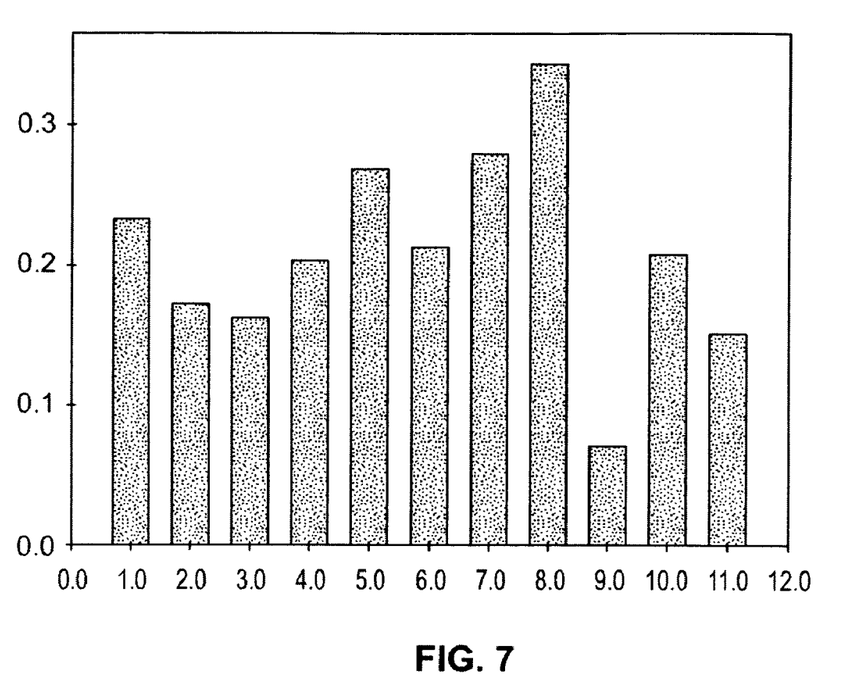
FIG. 7 is a front view of a computer screen showing another image containing a graphic of bars representing the signals provided by each sensor.
Figure 8:
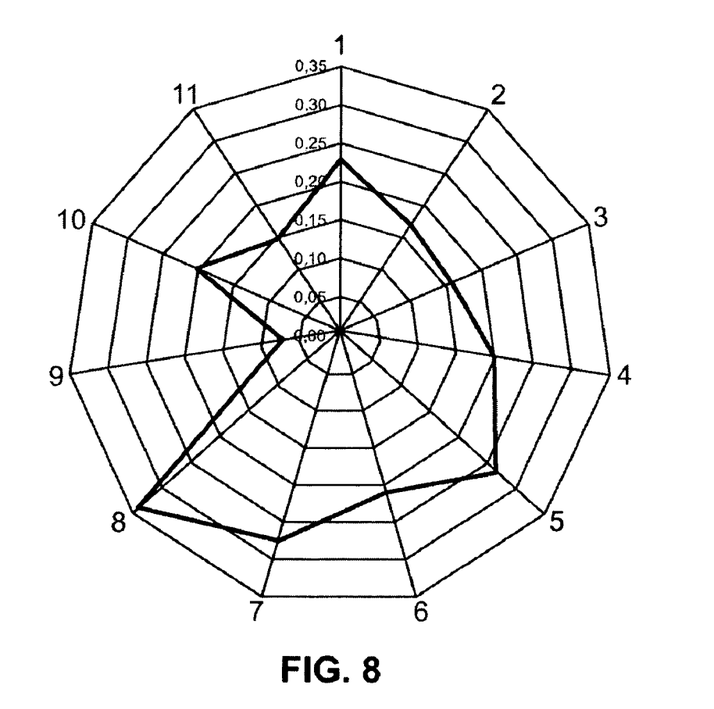
FIG. 8 is a front view of a computer screen showing another image containing a radar graphic representing the signals provided by the sensors.

The software provides the temporary displaying of base curves, measurements, bar charts, represented in FIG. 7, and/or radar graphs or charts, illustrated in FIG. 8.

The sensors signals versus the acquisition times may be exported to the store disc of the computer or the like by generating files in Excel-type tables or the like. The program provides the application for substracting files such as for substracting the data corresponding to a measurement and the measurements corresponding to a base line with the base line being a measurement taken with the chamber in standard status, such as without a sample or with a reference sample, in order to take reference values. The reference sample may be distilled water or a reference liquid. In this case the substraction is made for each time and for each sensor after having separately acquired the data corresponding to the measuring and the base line. Thus, with the signals obtained for each sensor in a predetermined acquisition time, bar charts and/or radar charts may be displayed.

The screens with the displaying of the software graphic inter-phase corresponding to the method of obtaining the data from the sample have been above disclosed. Now, the screens displaying the graphics or charts resulting from the analysis of the above data will be described.

Several methods and techniques for recognizing patterns, preferably Artificial Neural Networks and Principal Components Analysis, are employed. The analysis of principal components is a non-supervised method for reducing dimensionality and that permits discrimination of samples without supervision by means of the analysis of the covariance matrix. From said analysis the calculation of a set of variables named "principal components" is derived, thus a set for each measurement is obtained. Generally the three first principal components, PC1, PC2 and PC3, contain about the 99% of the total of data variation. The graph showing the PC1 points versus the PC2 points usually permits to discriminate the points associated to the several measurements, that is to the samples. The neural networks are no-lineal and generally supervised methods for classifying the data in pre-established groups. It requires of the computational training or setting of an artificial neural network and its further validation, by employing in both process, namely setting and validation, the data corresponding to previously obtained measurements contained in a data base.

Figure 9:
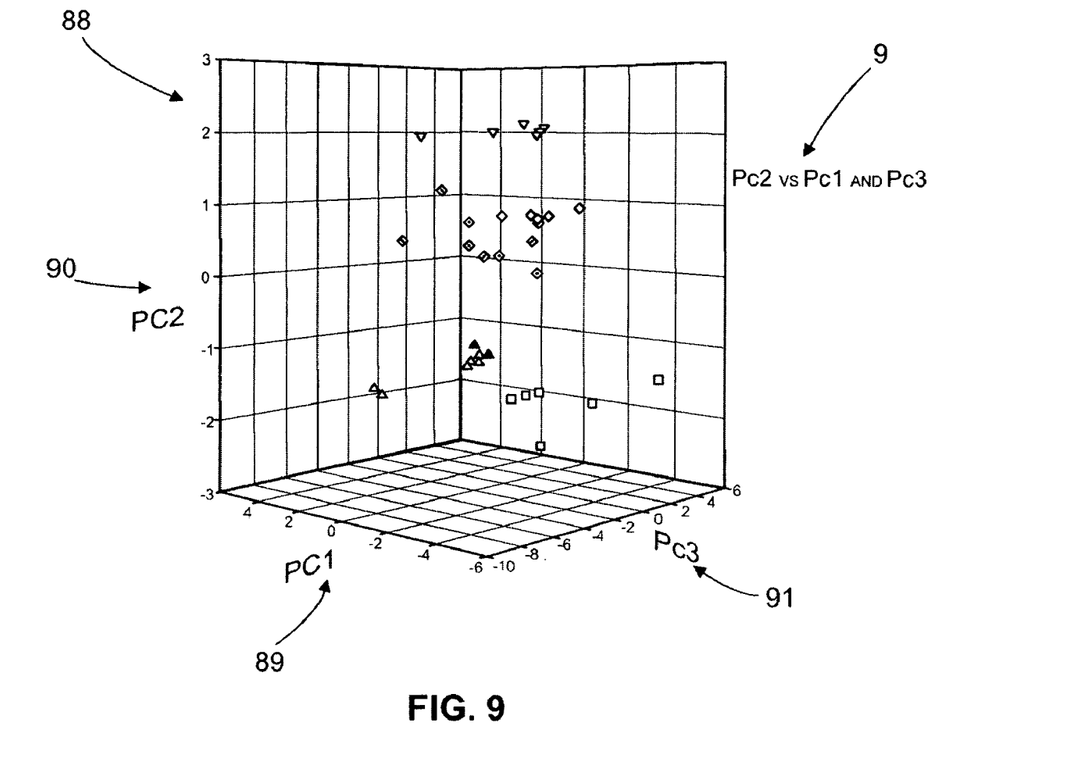
FIG. 9 is a front view of a computer screen showing another image containing a 3-D graphic representing the result of the analysis of the principal components (3 principal components).

FIG. 9 is a graph, which may be shown in a screen or display, showing a 3D-orthogonal graph 88 obtained from the analysis of the data by a method of analysis of principal components. In this case the three dimensions of the graph correspond to the principal components 1, 2 and 3, represented in the axes 89, 90 and 91, respectively. The software provides tools such as the box or window 92 for selection of principal components where the principal components desired to be graphed are indicated. Also it is possible to rotate the graph in several directions by the "move" tool 93 and to select the analysis criteria for obtaining the graph by using the analysis tool 94.

Figure 10:
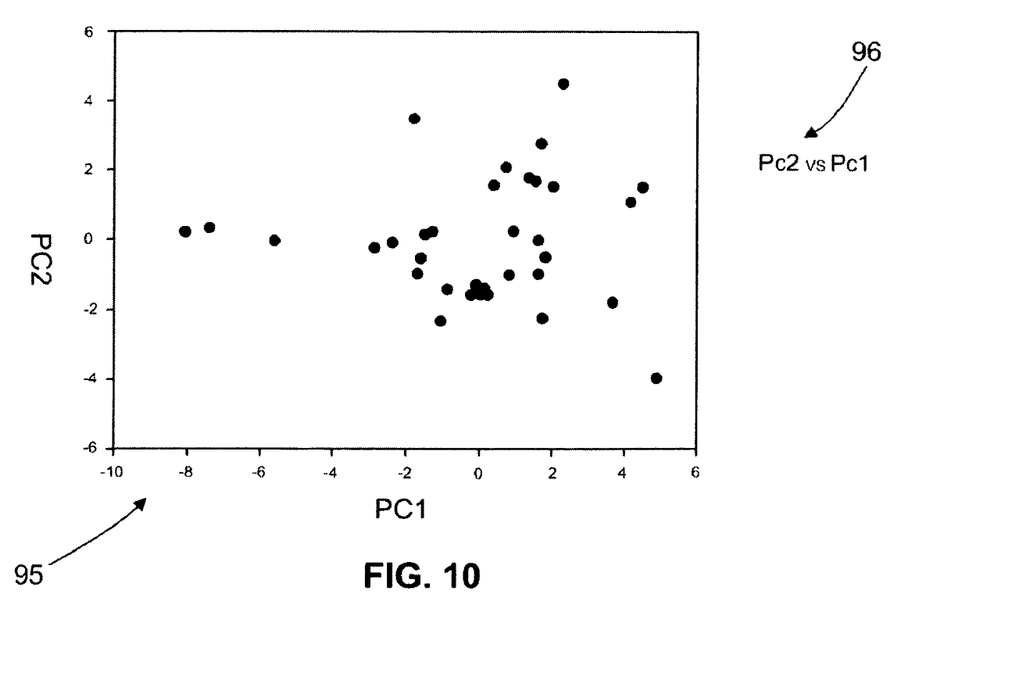
FIG. 10 is a front view of a computer screen showing another image containing a 2-D graphic representing the result of the analysis of the principal components (2 principal components).

FIG. 10 is a software screen or display showing a two dimension orthogonal graph 95 obtained from the analysis of data by using a method of analysis of principal components. Like in FIG. 9, the two dimensions of said graph correspond to the principal components 1 and 2, respectively. Basically, the screen or displaying of FIG. 10 is the same of FIG. 9 but with a selection in principal components box 96 distinct from the principal components selection in box 92 of FIG. 9.

The pattern recognizing programs hosted in computing 5 employ a data base with measurements previously obtained by the same equipment, from samples having well known characteristics, for comparing with the sample under analysis and obtaining the new results. For example, when analysing the "freshness" of a hake sample, the patterns correspond to measurements taken by the flavour-meter for a 1-day stored hake, for a 2-day stored hake, for a 3-day stored hake and so on, up to measures of a n-day stored sample with "n" depending on the criteria spectrum for the test. Then, once the values, namely the patterns, corresponding to the sample under analysis have been obtained the pattern recognizing programs compare these values with the already ones stored in the data base. In this way the storage time (days) of the hake under analysis is determined.

Figure 11:
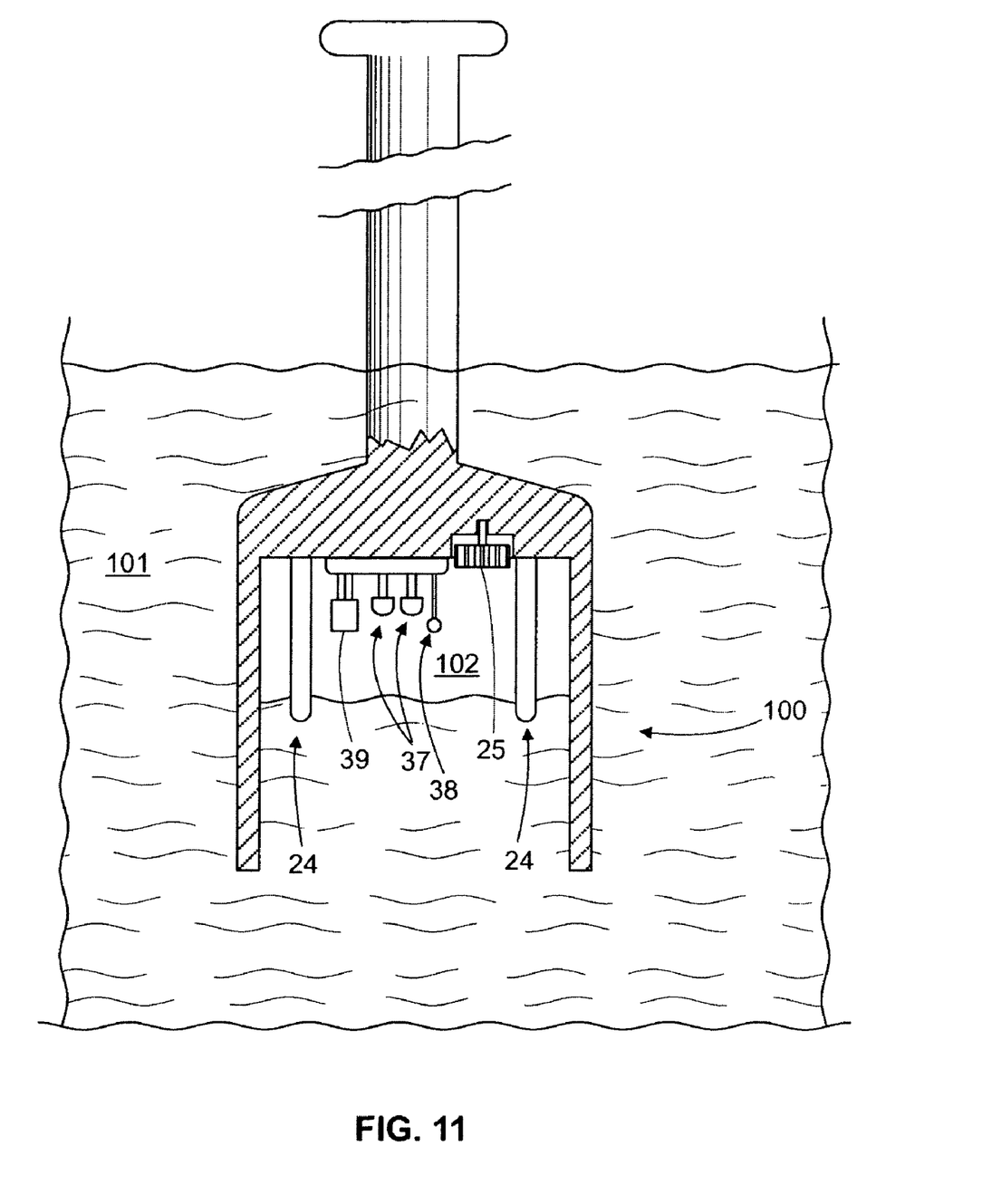
FIG. 11 is a side elevation and partial cross sectional view of another embodiment of the device according to the invention with the chamber being an inverted cup for introducing into a liquid to analyze the liquid in-situ.

Finally, FIG. 11 shows another embodiment of the invention wherein the chamber is comprised of an inverted cup 100 with the purpose of introducing the device into a liquid mass 101 such as into a wine cask or barrel, into industrial effluents, presumably contaminated water ways and any other liquid masses to be analyzed. The inventive device finds a useful application for determining the characteristics of a liquid mass in-situ without the need of taken a sample and bringing it into a laboratory. For this purpose cup 100 is provided with a sensors arrangement of the invention, as shown in FIGS. 2 and 3. Thus, cup 100 may be provided with vapour phase sensors 37, non-vapour phase sensors 24 designed and arranged to enter into contact with the liquid, temperature sensor 38, humidity sensor 39 and agitator 26. The design of cup 100 permits sensors 24 to be submerged into the liquid but sensors 37, 38, 39 and agitator 26 are prevented from entering into contact with the liquid. When inserted into the liquid mass and due to the inventive inverted-cup design, a gas mass 102 remains trapped into device 100 with gas 102 having all the characteristics of the environment close to the liquid surface. The level of liquid 101 within cup 100 or the volume of gas 102 may be easily foreseen according to the length of cup 100.

While preferred embodiments of the present invention have been illustrated and described, it will be obvious to those skilled in the art that various changes and modifications may be made therein without departing from the scope of the invention as defined in the appended claims.

I claim:

1. A device for analyzing matter containing volatile components, the device comprising:
    a chamber for receiving and containing a matter sample under stable thermal conditions;
    at least one first sensor arranged in the chamber for sensing a vapor phase of the sample;
    at least one second sensor arranged in the chamber for sensing a no-vapor phase of the sample;
    at least one third sensor arranged in the chamber for sensing temperature into the chamber;
    at least one fourth sensor arranged in the chamber for sensing humidity into the chamber;
    an electronic circuit connected to said sensors for a simultaneous and real time analysis of vapour and non-vapour phases of the sample, and
    a computing platform that comprises at least one pattern-recognizing program and/or a multivaried-data analysis program, wherein the electronic circuit simultaneously acquires data from the sensors and transmits the data to the computing platform so as to simultaneously evaluating odor and taste of the analyzed matter.

2. The device of claim 1, wherein the chamber is a closable container that when closed forms a sealed and watertight chamber for the sample.

3. The device of claim 2, wherein the sensors are mounted in at least one wall of the container.

4. The device of claim 3, wherein the container comprises an first portion and a second portion with both container portions being adjustably coupled to define at least a maximum distance position, a minimum distance position and a contact position between the sample and at least part of the sensors.

5. The device of claim 4, wherein the first and second portions of the container are threadably connected to regulate said positions between the sample and at least part of the sensors.

6. The device of claim 4, wherein at least one of the first and second portions of the container has a sliding connection to regulate said positions between the sample and at least part of the sensors.

7. The device of claim 4, wherein the chamber has at least one port for removing part of the sample and direct the same to a secondary analysis apparatus.

8. The device of claim 1, wherein at least one of the sensors is mounted in a mechanism for moving the at least one sensor towards to or away from the sample.

9. The device of claim 1, wherein at least one of the sensors and the sample is mounted in a mechanism for relatively moving the at least one sensor and the sample towards to or away from each other.

10. The device of claim 1, wherein an agitator is arranged in the chamber for agitating the vapour phase.

11. The device of claim 1, wherein a tray for containing the sample is arranged in the chamber.

12. The device of claim 1, wherein the chamber is connected to temperature control means to control the temperature into the chamber.

13. The device of claim 1, wherein the at least one first sensor and the at least one second sensor are of type selected from the group consisting of oxide-metal semiconductors, conductive polymers, oligomers, piezoelectric materials, surface acoustic wave sensors, noble metal electrodes, ion-selective electrodes, glass electrodes and the like.

14. The device of claim 1, wherein the at least one third sensor is of the type selected from the group consisting of thermistors, laser sensors, PT100 and thermocuples.

15. The device of claim 1, wherein the electronic circuit comprises a regulated voltage source, at least one load resistor connected to the sensors for sensing the vapour phase of the sample, and a control circuit for control, acquisition and transmission of data, the control circuit being connected to the at least one load resistor and including at least one high impedance adaptor connected to the sensors for sensing the no-vapour phase of the sample.

16. The device of claim 15, wherein the control circuit comprises at least one multiplexor connected to an analogical/digital converter that is connected to a micro controller, a clock circuit defining a timer circuit, and an adaptor circuit connected to a computer communications port and connected to said micro controller.

17. The device of claim 1, wherein the computing platform is communicated with the electronic circuit by means of a wire type connection.

18. The device of claim 1, wherein the computing platform is communicated with the electronic circuit by means of a wireless type connection.

19. The device of claim 1, wherein the chamber is a portable chamber.

20. The device of claim 19, wherein the portable chamber comprises an inverted cup for introducing into a liquid mass to be analyzed, with the at at least one first sensor being arranged at the top of the chamber to prevent the sensor to enter into contact with the liquid, wherein the at least one second sensor and the at least one third sensor extend from the top of the inverted cup for entering into contact with the liquid when the cup is introduced into the liquid mass, and wherein the at least one fourth sensor is arranged into the chamber to prevent the contact thereof with the liquid.

* * * * *